United States Patent
Tanaka et al.

(10) Patent No.: US 6,923,974 B2
(45) Date of Patent: Aug. 2, 2005

(54) FLAKY FINE POWDER, PRODUCTION THEREOF, AND COSMETIC

(75) Inventors: Hirokazu Tanaka, Kawasaki (JP); Naoyuki Enomoto, Kitakyushu (JP)

(73) Assignee: Catalysts & Chemicals Industries Co., Ltd., Tokyo (JP)

( * ) Notice: Subject to any disclaimer, the term of this patent is extended or adjusted under 35 U.S.C. 154(b) by 325 days.

(21) Appl. No.: 09/818,692

(22) Filed: Mar. 28, 2001

(65) Prior Publication Data

US 2002/0011186 A1 Jan. 31, 2002

Related U.S. Application Data (63) Continuation-in-part of application No. 08/671,943, filed on Jun. 28, 1996, now abandoned, which is a continuation of application No. 07/969,176, filed on Feb. 12, 1993, now abandoned.

(30) Foreign Application Priority Data

Aug. 16, 1990 (JP) .............................................. 2-216403

(51) Int. Cl.$^7$ ............................. A61K 6/00; A61K 7/00; A61K 9/16; A61K 33/00
(52) U.S. Cl. ....................... 424/401; 424/490; 424/489; 424/724
(58) Field of Search ................................ 424/401, 489, 424/490, 724

(56) References Cited

U.S. PATENT DOCUMENTS

| | | | | |
|---|---|---|---|---|
| 3,922,392 A | * | 11/1975 | Kohlschutter et al. | 427/215 |
| 4,509,988 A | * | 4/1985 | Bernhard | 106/308 |
| 5,407,746 A | * | 4/1995 | Prengel et al. | 428/403 |
| 5,478,550 A | * | 12/1995 | Suzuki et al. | 424/59 |
| 6,030,627 A | * | 2/2000 | Seo et al. | 424/401 |
| 6,309,627 B1 | * | 10/2001 | Golz-Berner et al. | 424/59 |
| 6,355,260 B1 | * | 3/2002 | Tanaka et al. | 424/401 |

* cited by examiner

*Primary Examiner*—Shaojia Anna Jiang
(74) *Attorney, Agent, or Firm*—Townsend & Banta (57) ABSTRACT

A flaky, fine powder comprising a flaky substance as the base and silica particles covering the surface of the base, aimed at reducing the glossiness of the base caused by the irregular reflection of light on its surface and improving the slipperiness. In particular, the powder comprises a flaky base substance such as natural mica and silica particles deposited on the base surface, wherein the silica particles may be optionally further immobilized by the hydrolysate of alkoxysilane or silica gel. The flaky fine powder is produced either by the adding alkoxysilane to a dispersion containing a flaky substance and silica particles and hydrolyzing it, by adding a silicic acid solution to the dispersion and gelling it, or by adding a combination of alkoxysilane and silicic acid solution. The powder can be compounded with various ingredients and is particularly useful with cosmetics.

18 Claims, 7 Drawing Sheets

FLAKY FINE POWDER, PRODUCTION THEREOF, AND COSMETIC

CROSS REFERENCE TO A RELATED APPLICATION

This is a continuation in part of U.S. application Ser. No. 08/671,943, filed Jun. 28, 1996, which is a continuation of U.S. application Ser. No. 07/969,176 filed Feb. 12, 1993, now abandoned.

BACKGROUND OF THE INVENTION

1. Field of the Invention

The present invention relates to a flaky, fine powder which is used as a mixing or compounding agent for cosmetics, pigments and paints, or as a filler for use with such materials as plastics, and production thereof. Furthermore, the present invention relates to cosmetics in which the aforesaid flaky, fine powder is mixed or compounded.

2. Description of Related Art

A flaky, fine powder has been used as a compounding agent for such materials as cosmetics, pigments and paints, or as a filler for such materials as plastics, and this type of flaky, fine powder, produced by covering the surface of a flaky substance such as mica as a base with metal oxide or other appropriate material is well known.

This type of flaky, fine powder is produced by precipitating hydroxide from aqueous solution of metallic salt under coexistence with a flaky substance as a base and depositing said hydroxide on the surface of the flaky substance.

However, a covering layer formed on the surface of the aforesaid flaky substance is a layer comprising primary particles and/or aggregated particles of the hydroxide and having an uneven thickness. For this reason, it is extremely difficult to control the form or thickness of the covered particles.

In addition, a main purpose of reduction of the conventional type of flaky, fine powder covered with oxides was to make use of the physical characteristics specific to the oxides used for covering the surface (such as a refractive index or a light transmittance), but a flaky, fine powder for use of its function originating from the shape of the covered particles has not been known.

In the German Patent Laid Open Publication No. 3922178 which was laid open on Jan. 17, 1991 after the priority date (Aug. 16, 1990) of the present PCT application, a minute flaky base which does not aggregate but has a high dispersibility, characterized in that said base contains spherical particles, each having a smaller diameter as compared to that of the minute flaky base, by at least 0.5% by weight, is disclosed. It is described in this publication that the minute flaky base having a diameter in a maximum range from 1 to 500 μm is suited, and that a diameter of the spherical particle should preferably be in the range from 0.05 to 50 μm.

It seems that the base can be easily moved because spherical particles act as a kind of ball bearing on the surface of the minute flaky substance.

Furthermore, in the aforesaid publication, the method of mixing a suspension of minute flaky base with a suspension of spherical particles, each having a smaller diameter as compared to that of the base, then filtering, drying, and calcining, if necessary, the base, is disclosed as the method of producing the aforesaid minute flaky base which does not aggregate and has a high dispersibility. Also, it is described in the publication that, when preparing the mixture described above, it is important to fully mix the two suspensions by means of ultrasonic processing.

SUMMARY OF THE INVENTION

Objects of the present invention include, by covering a surface of a flaky substance as a base with non-porous spherical particles to provide a means for reducing the glossiness of the base caused by the irregular reflection of light on its surface and improving the slipperiness of the base and to thus provide a new, and at the same time, useful, flaky, fine powder as well as a method for production thereof.

The flaky, fine powder according to the present invention comprises a flaky substance and silica particles deposited on its surface, or comprises the flaky substance and the silica particles further immobilized by hydrolysate of alkoxysilane or silica gel.

The flaky, fine powder according to one embodiment of the present invention is produced by adding alkoxysilane in a dispersion containing a flaky substance and silica particles and then hydrolyzing the alkoxysilane, or by adding silicic acid solution in the dispersion described above and gelling the silicic acid solution.

Furthermore, the production of the flaky, fine powder according to the present invention comprising depositing silica particles on a base in a dispersion, or immobilizing by hydrolysate of alkoxysilane and/or silica gel, is very simple and economical, and the non-porous spherical silica particles are tightly carried on the surface of the flaky substance, so that the flaky, fine powder is physically very stable and is available for various applications, as described above.

DESCRIPTION OF THE PREFERRED EMBODIMENTS

Description is made in detail for the flaky, fine powder according to the present invention and production thereof.

There is no restriction over a base in the present invention, as far as the substance is flaky or scalelike, and generally such materials as natural mica group including common mica, biotite, and sericite, or synthetic mica, talc, platelike silica, platelike titania, and glass flakes are available.

Appropriate thickness of a flaky substance is allowable for each application, but generally a flaky substance having thickness of approximately 1 μm or less is often used.

Silica particles deposited on a flaky substance are almost spherical, and an average particle size should preferably be approximately 5.0 μm or less, and particles having an average particle size in a range from about 0.05 to 3 μm are especially preferred. The average particle size refers to volume average particle size which are measured in accordance with JIS 2-8820 of Japanese Industrial Standard. The silica particles may comprise either only $SiO_2$ or compound oxide or mixture of the main component with one or more components other than $SiO_2$ such as $Al_2O_3$, $TiO_2$, $ZrO_2$, MgO, ZnO, $CeO_2$, or $Fe_2O_3$.

There is no specific restriction over the method of preparing silica particles and the method of dispersing the silica particles in a dispersion medium, and the silica particles are available in any form of hydrosol, organosol, or powder.

An operation to deposit silica particles on a surface of a base is carried out in a dispersion.

As a dispersion medium, water or organic solvent such as alcohol, glycol, ester, ketone or aromatic hydrocarbon solvent can be used independently or in combination thereof.

The operation for depositing silica particles on a surface of a flaky substance can be carried out in any of the following three ways.

(1) A base is added in a dispersion with silica particles dispersed therein, and then the dispersion is stirred.

(2) Silica particles are added in a dispersion with a base dispersed therein, and then the dispersion is stirred.

(3) Silica particles and a base are added simultaneously or one by one in a dispersion, and then the dispersion is stirred.

It is preferable that a dispersion, in which a flaky substance and silica particles are mixed and the two substances coexist, has the permittivity (∈) which is equal to or larger than 15 and equal to or smaller than 80 (15≦∈≦80), and in addition that the ion concentration (N) of the sum of cations and anions in the dispersion is in the following range:

1. When ∈ is equal to 15, 200 ppm≦N≦5×10$^4$ ppm.
2. When ∈ is equal to 80, 3×10$^4$ ppm≦N≦2×10$^5$ ppm.
3. When ∈ is larger than 15 but smaller than 80, N within a quadrilateral area formed with A (15, 200), B (15, 5×10$^4$), C (80, 2×10$^5$) and D (80, 3×10$^4$) in the (X, Y) coordinate system with the permittivity (∈) (–) on the X axis and the ion concentration (N) (ppm) on the Y axis.

Figure 1:
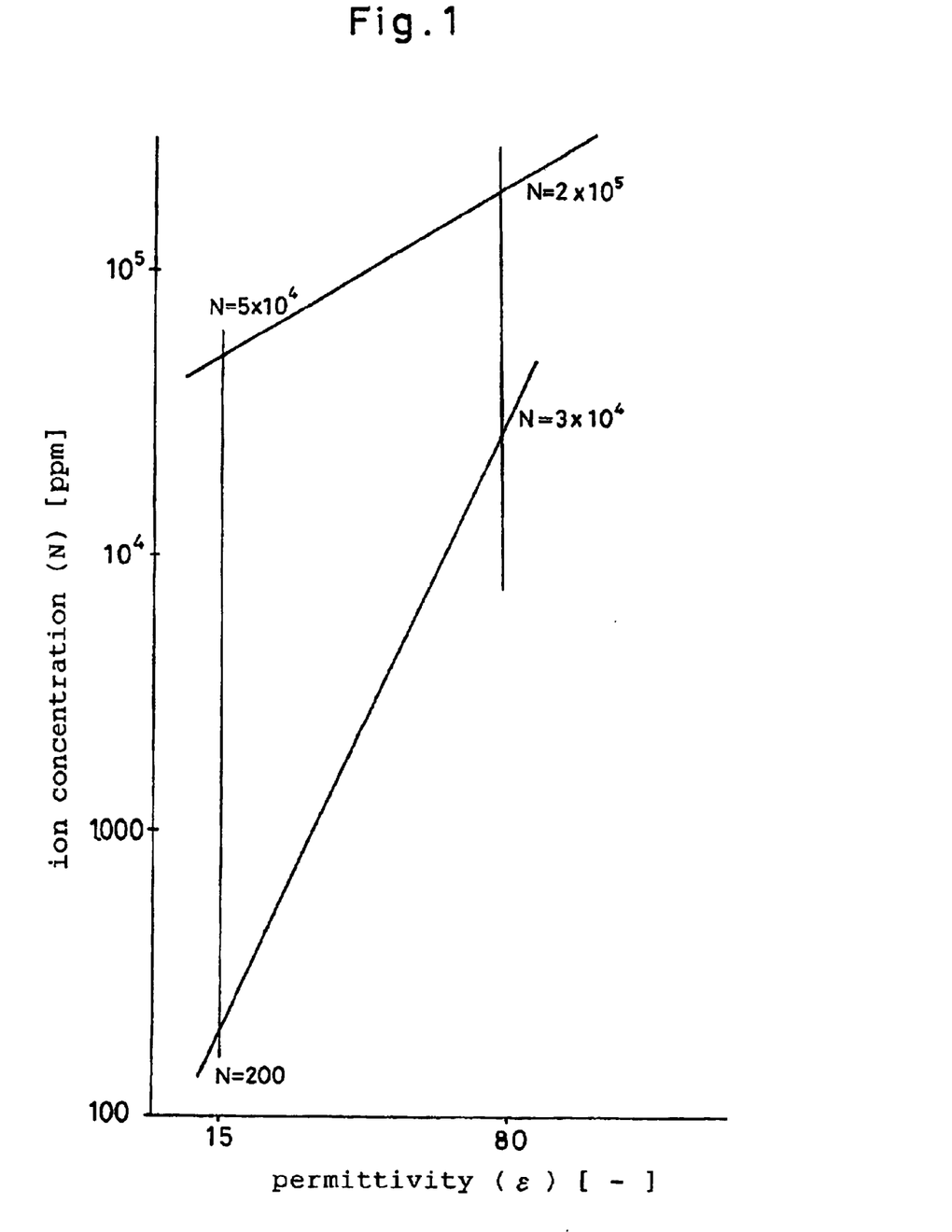
FIG. 1 is a drawing showing a preferred area of a dispersion when depositing silica particles on a flaky substance with the permittivity (∈)(–) in the horizontal axis and the ion concentration (N) (ppm) in the vertical axis.

FIG. 1 shows the area described above with the permittivity (∈) (–) on the horizontal axis and the ion concentration (N) (ppm) on the vertical axis.

If ∈ and N are within this range, silica particles adhere on the flaky substance in the dispersion, and cover its surface with about a single layer.

The permittivity of a dispersion and ion concentration (N) in the dispersion are controlled within this range by, for instance, deionizing the dispersion or adding such ions as alkali.

It is not always required that particle size of silica particles is homogeneous in the processing for deposition. Even if particles with different diameter coexist, silica particles adhere without causing any specific problem, so long as the particle size is 5.0 μm or less. Also, silica particles having a particle size of more than 5.0 μm adhere, but easily separate from a surface of a base. Also, sometimes silica particles adhere on the surface of the base and form multiple layers there, but adhesive strength of silica particles other than those directly adhered on the surface of the base is extremely weak, so that the particles easily separate from the surface.

There is no specific restriction over the concentration of solids in a dispersion in which silica particles and base are mixed, so long as the concentration does not cause any trouble to such operations as stirring, but preferably it should be not more than 70% by weight.

In the present invention, it is not necessary that the entire surface of a base is covered with silica particles. A quantity of silica particles to be added against a quantity of a base is selected within a quantity of silica particles required to completely cover the entire surface of the base according to the purpose of each application.

Flaky, fine powder covered with silica particles can be obtained by filtering, washing, and drying the dispersion after the aforesaid operation for deposition.

The flaky, fine powder obtained as described above is in a state where silica particles have adhered to the surface of the base, and not in a state where the silica particles have been immobilized to the surface. For this reason, if it is desired to provide a flaky, fine powder with silica particles tightly immobilized to the surface of the base, or when it is desired that silica particles hardly separate from the surface of the base so as, for instance, to achieve the soft focus effective in cosmetics, it is necessary to immobilize silica particles on the surface of the base.

In the present invention, a process for immobilizing silica particles on a surface of a base is carried out by using alkoxysilane or silicic acid solution.

It should be noted that the process for immobilizing silica particles may be carried out immediately after the aforesaid process for deposition, and also that the process for deposition and the process for immobilizing silica particles may be carried out simultaneously.

When alkoxysilane is used as a fixing agent, alkoxysilane is added in the aforesaid dispersion, and then the alkoxysilane is hydrolyzed.

If alkoxysilane is to be added, it is preferable to use tetraalkoxysilane. Tetraalkoxysilane is generally expressed by the chemical formula of $Si(OR)_4$, and the R indicates an alkyl group with a carbon number of 1 to 7. Concretely, tetramethoxysilane, tetraethoxysilane and tetraisopropoxysilane are included in this group.

A quantity of alkoxysilane to be added varies according to the adhesive strength of silica particles required in each application of the flaky, fine powder. Concretely, the quantity can be obtained by estimating a quantity of alkoxysilane in terms of $SiO_2$, required for a hydrolysate of alkoxysilane to fill clearance between silica particles deposited on a surface of a base with a certain thickness.

The adhesive strength of silica particles becomes stronger as the quantity of hydrolysate used to fill the clearance between silica particles increases, but even if the quantity exceeds a particle size of the silica particles, the adhesive strength does not become higher than a certain level.

There is no specific restriction over the condition of hydrolysis of tetraalkoxysilane, and it may be carried out under conventional conditions. For instance, a dispersion, in which tetraalkoxysilane has been added, is hydrolyzed at a temperature in a range from about 20° C. to about 150° C.

Then, to promote the hydrolysis of alkoxysilane, alkali or acid may be added as a catalyst. As an alkali catalyst, such a material as ammonia, hydroxide of alkali metal, or amines is available. Also, as an acid catalyst, various types of organic acid or inorganic acid can be used.

As described above, an operation for immobilizing silica particles may be carried out by using silicic acid solution, and herein the silicic acid solution is an aqueous solution of a low grade polymer of silicic acid dealkalized by means of ion-exchanging an aqueous solution of alkali metal silicate such as water glass. If the dispersion medium is water itself or the percentage of water in it is high, a process using silicic acid solution is recommended.

The silicic acid solution is polymerized or gelled by adding a specified quantity of this silicic acid solution in a dispersion in which a flaky substance has been dispersed to fill clearance between silica particles with silica gel. Silica particles are immobilized to the surface of the base by the silica gel.

It should be noted that it is possible to carry out the processing for immobilizing silica particles by simultaneously using silicic acid solution and alkoxysilane.

Also, it should be noted that the conditions concerning the permittivity ($\in$) and the ion concentration (N) for a dispersion in the aforesaid process for deposition are not applicable to the process for immobilizing silica particles. Namely, so long as silica particles are immobilized to a surface of a base to some degree by means of operation for immobilizing them after adhesion, the dispersion may not always satisfy these conditions.

After the process for immobilizing silica particles as described above is finished, flaky, fine powder with silica particles deposited on a surface and simultaneously immobilized with hydrolysate of alkoxysilane and/or silica gel can be obtained by filtering, washing and drying the dispersion phase. Furthermore, this flaky, fine powder may be calcined, if necessary.

The flaky, fine powder obtained thus can be compounded in cosmetics in which powder is generally used, in the same way as that for compounding a conventional type of inorganic pigment in it, as it is, or after additional surface treatment with a known agent according to the need.

Examples of this type of cosmetic include cosmetics such as liquid foundation, powder foundation, cake foundation, stick foundation, face powder, lip stick, rouge, eye liner, eye shadow, eyebrow pencil, and, in addition, body powder, anhidrotics, sunblock, solid white powder, milk lotion, and lotion. These types of cosmetics are excellent in feeling when used for applying and spreading on skin as well as in cosmetic finishing effect such as so-called soft focus effect, for instance, to make wrinkles invisible.

The surface treatment described above is generally carried out by using silane coupling agent. Also, processing with such a material as silicone oil, fluorine-based oil containing perfluoro alkyl group, higher fatty acid or salt thereof, ester of higher fatty acid to improve the water resistance and sweat resistance, or processing with such a material as lecithin, hydrogenated lecithin, acylamino acid, or peptide, is useful for this purpose.

A compounding ratio of the flaky, fine powder against the cosmetic as described above is freely selected according to characteristics of each cosmetic, and the ratio is about 0.5 to 40% by weight, for instance, in liquid foundation, about 1 to 80% by weight in cake foundation, about 1.5 to 85% by weight in powder foundation, about 1 to 95% by weight in face powder, and about 0.5 to 20% by weight in cream, and generally a range from about 0.5 to 95% by weight, and preferably of about 2 to 85% by weight against the cosmetic as a whole is selected.

Various types of components which are generally used in cosmetics, oils such as higher aliphatic alcohol, higher fatty acid, ester oil, paraffin oil, and wax; alcohol such as ethyl alcohol propylene glycol, sorbitol, and glucose; mucopolysaccharide, agents for maintaining humidity such as PCA salt or lactate, various types of surfactant including nonionic, cationic, anionic, and amphoteric ones; thickeners such as gum arabic, xanthan, polyvinyl pyrolidone, ethyl cellulose, carboxymethyl cellulose, carboxyvinyl polymer, metamoriphic or non-metamoriphic clay minerals; solvent such as ethyl acetate, acetone, toluene; inorganic or organic pigment or dyestuff; antioxidant such as BHT and tocopherol; water, chemicals, ultraviolet ray absorbent, pH buffer solution comprising salt of an organic acid or an inorganic acid; chelating agent, antiseptic agent, perfume or other materials are selected and mixed in the aforesaid cosmetic according to the necessity.

Detailed description was made above for a case where the flaky, fine powder is compounded in cosmetics, but the flaky, fine powder according to the present invention is not limited to use in cosmetics and can be used as a compounding agent for pigment or flat paint, or as a filler for such materials as plastic independently or in combination with other materials as previously described.

Detailed description is made hereinafter with reference to related experiments, but it should be noted that these experiments are introduced only as examples. When producing the flaky, fine powder, in addition to the conditions employed in the experiments described below, the average particle size of silica particles may be changed, and alkoxysilane other than tetraethoxysilane or tetramethoxysilane may be used. For this reason, the present invention should not be limited in scope to the results of these experiments. The scope of the present invention is defined by claims. Also, any alteration or change constituting an equivalent claim shall be regarded as within the scope of the present invention.

EXAMPLE 1

A mixed liquid was prepared by mixing 100 g of silica organosol prepared by dispersing $SiO_2$ particles, each having an average particle size of 0.6 $\mu$m, in monoethylene glycol as a dispersion medium with a $SiO_2$ concentration of 20% by weight with 220 g of isopropanol. 80 g of natural mica having a thickness of 0.3 $\mu$m and aspect ratio of 100 was added in this mixed liquid, and then 500 g of ethanol was added, stirring the liquid at room temperature, and additionally the pH was adjusted to more than 9.5 by adding 28% aqueous ammonia in the liquid to adhere silica particles on the surface of the mica.

The permittivity ($\in$), the ion concentration (N), and the concentration of solids of this dispersion are shown in Table 1 together with values in other examples described hereinafter.

In the examples of the present invention, the permittivity ($\in$) at 25° C. was obtained by measuring a refraction index (n) of the dispersion and calculating through the following equation, assuming that dielectric loss does not occur.

$$\in = n^2$$

In the experiments, a refraction index meter Model RX-1000 produced by ATAGO Co., Ltd. was used, and measurement was carried out at 25° C.

The ion concentration (N) in each dispersion was measured by centrifuging 50 ml of a dispersion for 30 minutes at 3000 rpm and sampling the supernatant.

Measurement of the concentration of ammonium ions was carried out by means of the Kjeldahl method, while measurement of the concentration of cations such as sodium ions, calcium ions, and aluminum ions was carried out by atomic absorption spectrometry (by using a polarized Zeeman atomic absorption photometer produced by Hitachi, Ltd., Model 180-80) and measurement of the concentration of anions such as chloride ions, sulfate ions, and nitrate ions was carried out by means of ion chromatography (produced by DIONEX, 2010i).

Then, this dispersion was heated to 45° C., and tetraethoxysilane and 28% aqueous ammonia were added simultaneously for 5 hours, maintaining the aforesaid temperature and pH. A quantity of added tetraethoxysilane was 13.3 g in terms of $SiO_2$, and a quantity of added aqueous ammonia was 153 g.

After addition of the materials was finished, the mixture was additionally stirred for 2 hours, the dispersion was filtered, washed and then dried at 100° C., and furthermore calcined for 4 hours at 600° C., and thus flaky, fine powder with silica particles immobilized on the surface of the mica in about a single layer was obtained.

Figure 2:
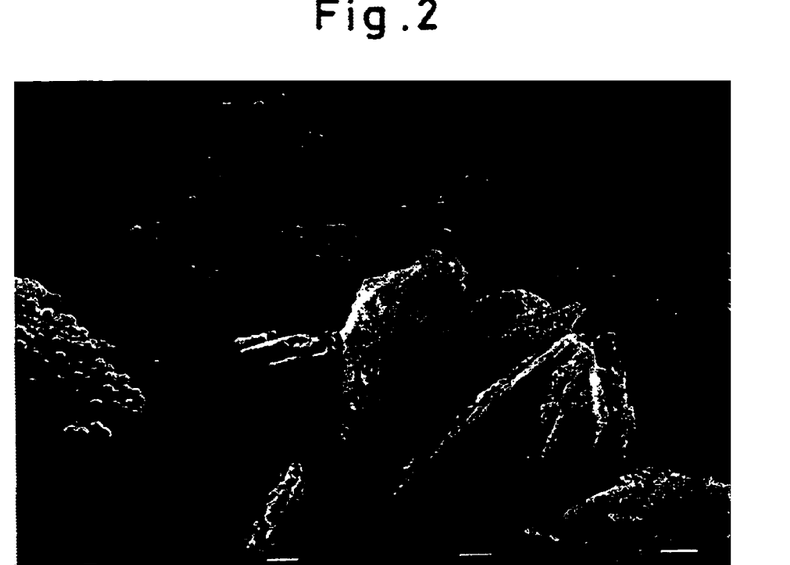
FIG. 2 and FIG. 3 are photographs showing the structure of particles on the surface of the flaky, fine powders obtained in Example 1 and Example 21, respectively.

An electron microscopic picture of the flaky, fine powder (magnified by 3500 times) is shown in FIG. 2.

An analysis of the spherical silica (SS-160P) as used in this example of our invention was made and the following data was obtained:

(a) Average particle size of $SiO_2$: 0.15 μm (Centrifugal particle size analyzing method)
(b) Specific surface area of $SiO_2$: 18 $m^2/g$ (BET: $N_2$ gas adsorption method)

In addition, the geometric surface area of the silica was calculated at 18.2 $m^2/g$ as follows:

Calculation of the Geometric Surface Area of Silica Particles

SA: specific surface area
N: the number of particles per gram
A: surface area of a spherical particle $$SA = N \times A$$

$$N = \frac{1}{\lambda} / \left( \frac{4\pi r^2}{3} \right) = \frac{3}{4\pi r^2 \lambda} \; [/g]$$

(λ: density, r: radius of particles)

$$A = 4\pi r^2 \; [m^2]$$

$$\therefore SA = 4\pi r^2 \times \frac{3}{4\pi r^2 \lambda} = \frac{3}{\lambda r} \; [m^2/g]$$

$\lambda$(SS-160P)=2.2 $g/cm^3$=2.2×$10^4$ $g/m^2$ $r$(SS-160P)=0.075 μm=0.075×$10^{-4}$ m $$\therefore SA = \frac{3}{2.2 \times 10^4 \times 0.075 \times 10^{-4}} = 18.2 \; [m^2/g]$$

It can be seen that the calculated surface area is almost the same as the analyzed surface area, showing that the sample of the spherical silica is non-porous. (If the silica is porous, the analyzed surface area would be relatively larger than the calculated surface area.)

EXAMPLE 2

The procedures were carried out in the same manner as described in Example 1 except that ethanol was used instead of isopropanol used in Example 1, and flaky, fine powder was obtained. By electron microscope observation, it was confirmed that spherical silica particles were immobilized on the surface of the natural mica in about a single layer similar to FIG. 2.

EXAMPLE 3

The procedures were carried out in the same manner as described in Example 1 except that 1,3-butylene glycol was used instead of monoethylene glycol used in Example 1, and flaky, fine powder was obtained. By electron microscope observation, it was confirmed that spherical silica particles were immobilized on the surface of the natural mica in about a single layer similar to FIG. 2.

EXAMPLE 4

The procedures were carried out in the same manner as described in Example 1 except that ethanol was used instead of monoethylene glycol used in Example 1, and flaky, fine powder was obtained. By electron microscope observation, it was confirmed that spherical silica particles were immobilized on the surface of the natural mica in about a single layer similar to FIG. 2.

EXAMPLE 5

The procedures were carried out in the same manner as described in Example 1 except that tetramethoxysilane was used instead of tetraethoxysilane used in Example 1, and flaky, fine powder was obtained. By electron microscope observation, it was confirmed that spherical silica particles were immobilized on the surface of the natural mica in about a single layer similar to FIG. 2.

EXAMPLE 6

The procedures were carried out in the same manner as described in Example 1 except that $SiO_2$ particles having an average particle size of 0.3 μm were used, and flaky, fine powder was obtained. By electron microscope observation, it was confirmed that spherical silica particles were immobilized on the surface of the natural mica in about a single layer similar to FIG. 2.

EXAMPLE 7

The procedures were carried out in the same manner as described in Example 1 except that silica organosol in which $SiO_2$ particles having an average particle size of 1.0 μm were dispersed and which has a $SiO_2$ concentration of 60% by weight was used, and flaky, fine powder was obtained. By electron microscope observation, it was confirmed that spherical silica particles were immobilized on the surface of the natural mica in about a single layer similar to FIG. 2.

EXAMPLE 8

The procedures were carried out in the same manner as described in Example 1 except that 1,3-butylene glycol was used instead of monoethylene glycol used in Example 1, and that n-butanol was used instead of ethanol used in Example 1, and flaky, fine powder was obtained. By electron microscope observation, it was confirmed that spherical silica particles were immobilized on the surface of the natural mica in about a single layer similar to FIG. 2.

EXAMPLE 9

The procedures were carried out in the same manner as described in Example 1 except that 1,3-butylene glycol was used instead of monoethylene glycol used in Example 1, and that acetone was used instead of ethanol used in Example 1, and flaky, fine powder was obtained. By electron microscope observation, it was confirmed that spherical silica particles were immobilized on the surface of the natural mica in about a single layer similar to FIG. 2.

EXAMPLE 10

The procedures were carried out in the same manner as described in Example 1 except that silica organosol having a $SiO_2$ concentration of 40% by weight was used, and that 60 g of natural mica was used without the isopropanol in Example 1, and flaky, fine powder was obtained. By electron microscope observation, it was confirmed that spherical silica particles were immobilized on the surface of the natural mica in about a single layer similar to FIG. 2.

EXAMPLE 11

The procedures were carried out in the same manner as described in Example 1 except that the ethanol was not added in the mixed liquid, and that the liquid was heated to 35° C., and flaky, fine powder was obtained. By electron microscope observation, it was confirmed that spherical silica particles were immobilized on the surface of the natural mica in about a single layer similar to FIG. 2.

EXAMPLE 12

The procedures were carried out in the same manner as described in Example 11 except that silica organosol having a $SiO_2$ concentration of 40% by weight was used, and that 160 g of natural mica was used, and flaky, fine powder was obtained. By electron microscope observation, it was confirmed that spherical silica particles were immobilized on the surface of the natural mica in about a single layer similar to FIG. 2.

EXAMPLE 13

Mixed liquid was prepared by mixing 200 g of silica hydrosol prepared by dispersing $SiO_2$ particles, each having an average particle size of 0.3 μm, in water as a dispersion medium with a $SiO_2$ concentration of 10% by weight with 220 g of methanol. 80 g of talc having a thickness of 0.4 μm and aspect ratio of 120 was added in this mixed liquid, and then to adjust pH of more than 12.5, 28% aqueous ammonia was added, stirring this liquid at the room temperature, to adhere silica particles on the surface of the talc.

Then, this dispersion was heated to 35° C., and maintaining the temperature and the aforesaid pH, the procedures for immobilizing by using tetraethoxysilane and 28% aqueous ammonia were carried out in the same manner as described in Example 1, and thus flaky, fine powder with silica particles immobilized on the surface of the talc in about a single layer similar to FIG. 2 was obtained.

EXAMPLE 14

Mixed liquid was prepared by mixing 100 g of silica organosol prepared by dispersing $SiO_2$ particles, each having an average particle size of 0.1 μm, in monoethylene glycol as a dispersion medium with a $SiO_2$ concentration of 20% by weight with 220 g of isopropanol. 180 g of natural mica having a thickness of 0.3 μm and aspect ratio of 100 was added in this mixed liquid, and then 500 g of water was added, stirring this liquid at the room temperature and, additionally, pH was adjusted to more than 11.0 by adding 28% aqueous ammonia in the liquid to adhere silica particles on the surface of the mica.

Then, this dispersion was heated to 45° C., and maintaining the temperature and the aforesaid pH, the procedures for immobilizing by using tetraethoxysilane and 28% aqueous ammonia were carried out in the same manner as described in Example 1, and thus flaky, fine powder with silica particles immobilized on the surface of the mica in about a single layer similar to FIG. 2 was obtained.

EXAMPLE 15

The procedures were carried out in the same manner as described in Example 13 except that tetramethoxysilane was used instead of tetraethoxysilane used in Example 13, and flaky, fine powder was obtained. By electron microscope observation, it was confirmed that spherical silica particles were immobilized on the surface of the talc in about a single layer similar to FIG. 2.

EXAMPLE 16

The procedures were carried out in the same manner as described in Example 11 except that 45 g (as $SiO_2$) of tetraethoxysilane was used, and flaky, fine powder was obtained. By electron microscope observation, it was confirmed that spherical silica particles were immobilized on the surface of the natural mica in about a single layer similar to FIG. 2.

EXAMPLE 17

Mixed liquid was prepared by mixing 100 g of silica organosol prepared by dispersing $SiO_2$ particles, each having an average particle size of 0.6 μm, in monoethylene glycol as a dispersion medium with a $SiO_2$ concentration of 20% by weight with 220 g of isopropanol. 80 g of platelike silica having a thickness of 0.5 μm and aspect ratio of 90 was added in this mixed liquid, simultaneously with a mixed liquid comprising 13.3 g of tetraethoxysilane in terms of $SiO_2$ and 500 g of water, and additionally pH was adjusted to 11.0 by adding 28% aqueous ammonia in this liquid, maintaining this pH and the temperature of 25° C., the liquid was stirred for 2 hours.

After the aforesaid procedures, the dispersion was filtered, washed and then dried at 110° C., and furthermore calcined for 4 hours at 600° C., and thus flaky, fine powder with silica particles immobilized on the surface of the platelike silica in about a single layer similar to FIG. 2 was obtained.

EXAMPLE 18

The procedures were carried out in the same manner as described in Example 17 except that tetraisopropoxysilane was used instead of tetraethoxysilane used in Example 17, and flaky, fine powder was obtained. By electron microscope observation, it was confirmed that spherical silica particles were immobilized on the surface of the platelike silica in about a single layer similar to FIG. 2.

EXAMPLE 19

80 g of natural mica having a thickness of 0.3 μm and aspect ratio of 100 was added in a 100 g of silica hydrosol prepared by dispersing $SiO_2$ particles, each having an average particle size of 0.6 μm, in water as a dispersion medium with a $SiO_2$ concentration of 20% by weight, and then 83 g of 17.1% aqueous solution of sodium hydroxide was added, stirring the liquid at the room temperature, to adhere silica particles on the surface of the mica.

Then, 91 g of silicic acid solution with a $SiO_2$ concentration of 5% by weight was added in the dispersion, and maintaining the temperature of 95° C., the procedures were carried out in accordance with Example 1, and thus flaky, fine powder with silica particles immobilized on the surface of the mica in about a single layer similar to FIG. 2 was obtained.

EXAMPLE 20

80 g of natural mica used in Example 19 and 67 g of silicic acid solution with a $SiO_2$ concentration of 5% by weight were added simultaneously in 100 g of silica hydrosol used in Example 19, and then 246 g of 25% aqueous solution of sodium hydroxide was added in the dispersion, the procedures were carried out in the same manner as described in Example 19, and thus flaky, fine powder with silica particles immobilized on the surface of the mica in about a single layer similar to FIG. 2 was obtained.

EXAMPLE 21

Mixed liquid was prepared by mixing 100 g of silica organosol prepared by dispersing $SiO_2$ particles, each having an average particle size of 0.6 $\mu$m, in monoethylene glycol as a dispersion medium with a $SiO_2$ concentration of 20% by weight with 220 g of isopropanol. 80 g of natural mica used in Example 1 was added in this mixed liquid, and then 500 g of ethanol was added, stirring this liquid at the room temperature, and additionally pH was adjusted to more than 9.5 by adding 28% aqueous ammonia in the liquid to adhere silica particles on the surface of the mica.

After the aforesaid procedures, the dispersion was filtered and then dried at 110° C., and thus flaky, fine powder covered with silica particles was obtained.

Figure 3:
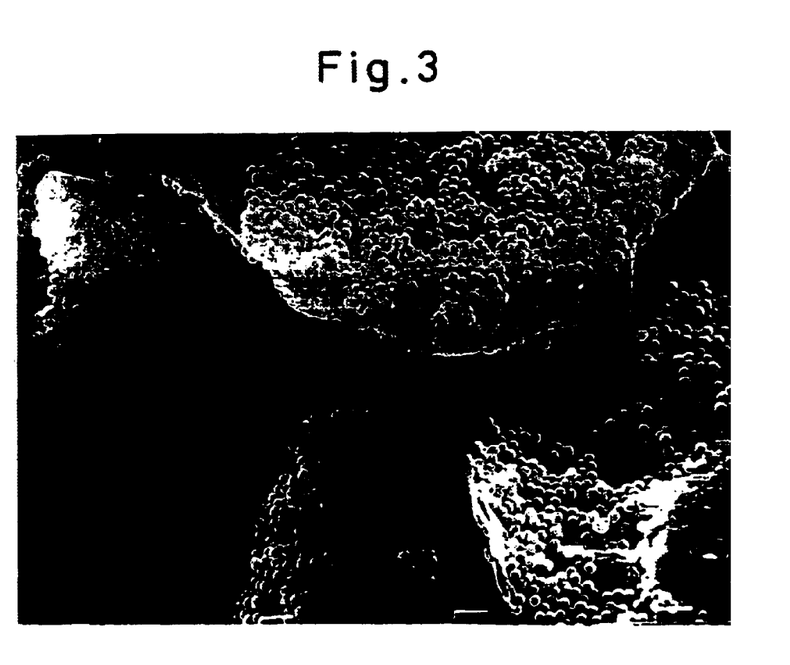

An electron microscopic picture of the flaky, fine powder (magnified by 3500 times) is shown in FIG. 3.

TABLE 1

| Example No. | Permittivity (-) | Ion concn. (ppm) | Concn. of solids (wt. %) |
|---|---|---|---|
| 1 | 24.6 | 860 | 11.1 |
| 2 | 25.8 | 860 | 11.1 |
| 3 | 24.0 | 860 | 11.1 |
| 4 | 23.3 | 860 | 11.1 |
| 5 | 24.6 | 860 | 11.1 |
| 6 | 24.6 | 860 | 11.1 |
| 7 | 23.9 | 720 | 15.5 |
| 8 | 19.5 | 860 | 11.1 |
| 9 | 21.7 | 860 | 11.1 |
| 10 | 27.5 | 13730 | 14.5 |
| 11 | 31.4 | 50740 | 21.4 |
| 12 | 32.2 | 61780 | 35.7 |
| 13 | 55.1 | 65240 | 16.1 |
| 14 | 55.8 | 14380 | 19.1 |
| 15 | 55.1 | 65240 | 16.1 |
| 16 | 31.4 | 50640 | 21.4 |
| 17 | 25.2 | 13090 | 10.1 |
| 18 | 24.9 | 13070 | 10.0 |
| 19 | 78.5 | 49240 | 38.0 |
| 20 | 78.5 | 90120 | 21.0 |
| 21 | 24.6 | 860 | 11.1 |

Fixing Test of Silica Particles

Water dispersion containing flaky, fine powder obtained in Example 1 or Example 21, respectively, were stirred for about 10 hours by a mixer, and samples of the fine powder were observed by means of an electron microscope.

Figure 4:
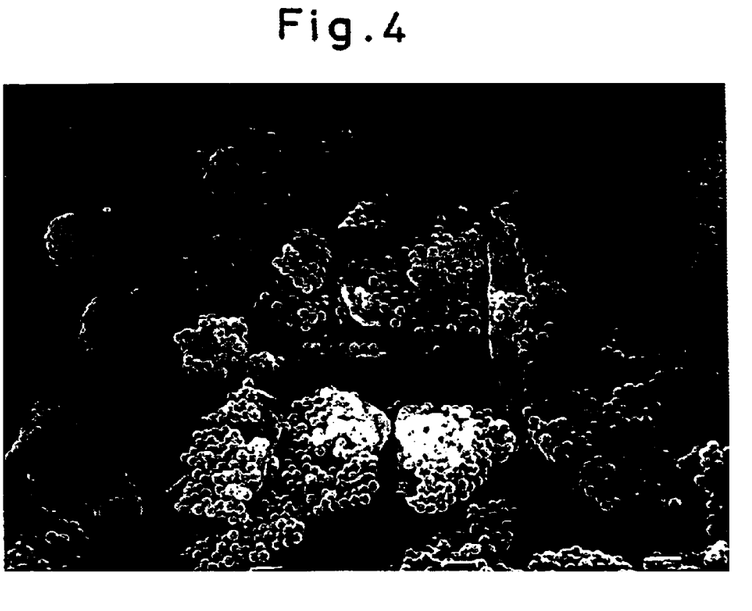
FIG. 4 and FIG. 5 are photographs showing the structure of particles on the surface of the flaky, fine powders obtained in Example 1 and Example 21, respectively, after the samples underwent the fixing test.
Figure 5:
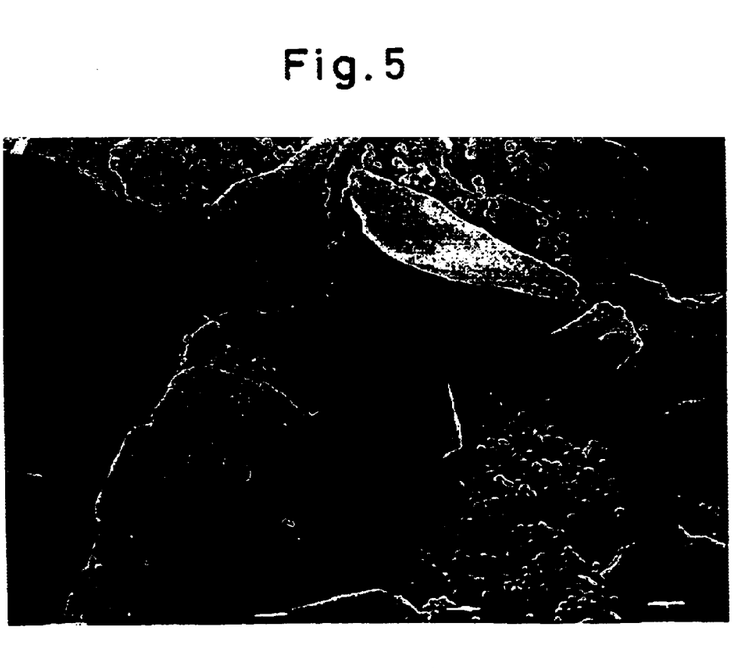
Figure 6:
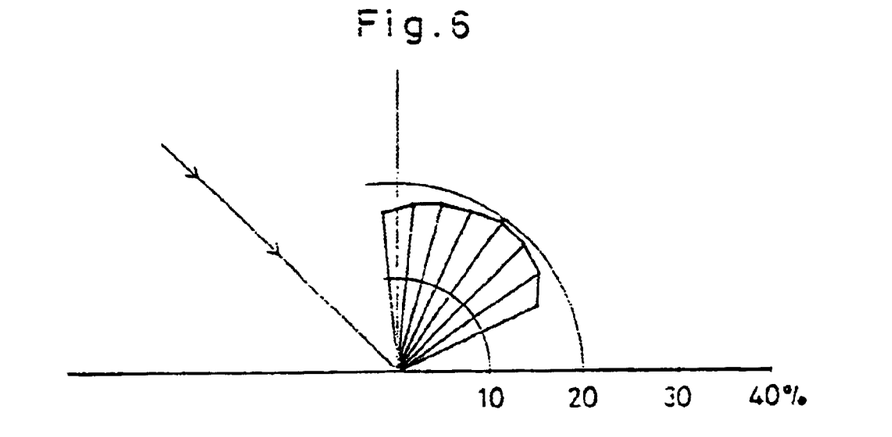
FIG. 6 through FIG. 10 are drawings of reflected light distributions showing the scattering of reflected light when light is irradiated on samples A to E, respectively.
Figure 7:
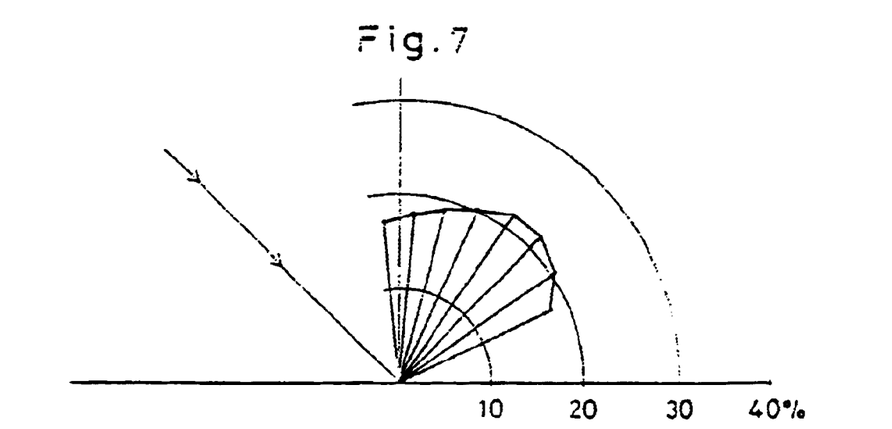
Figure 8:
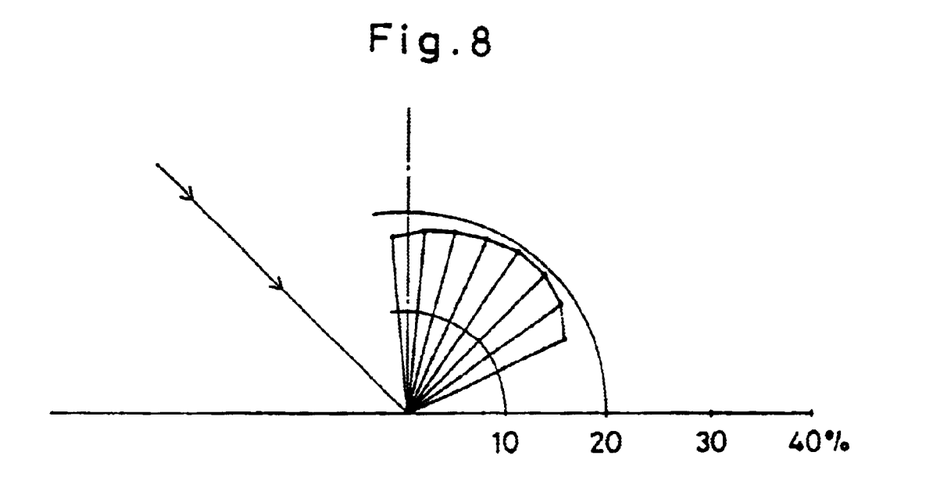
Figure 9:
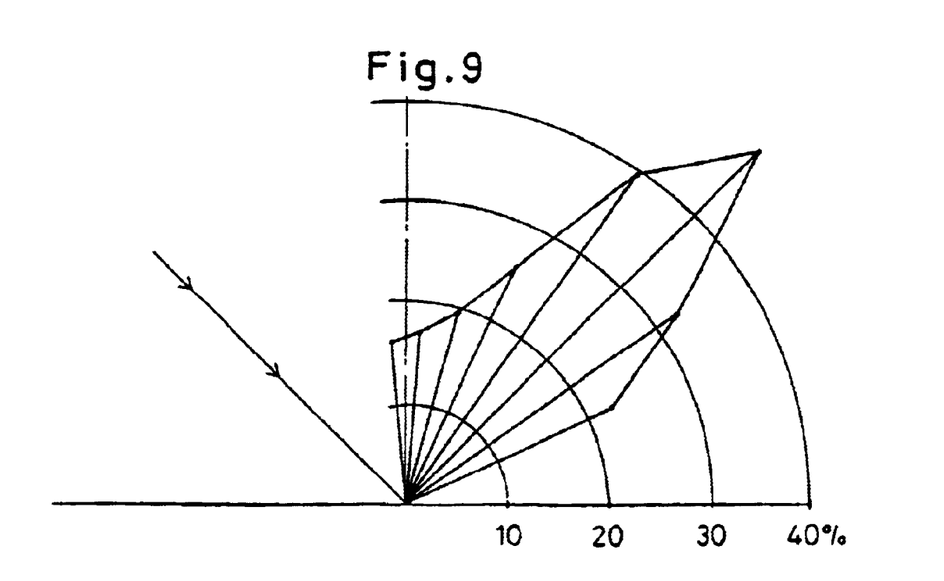
Figure 10:
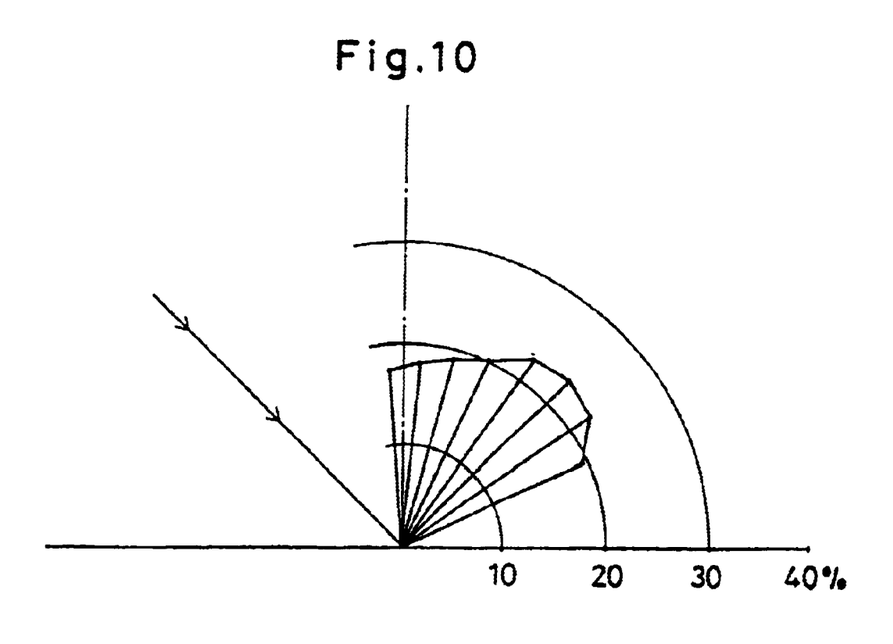
Figure 11:
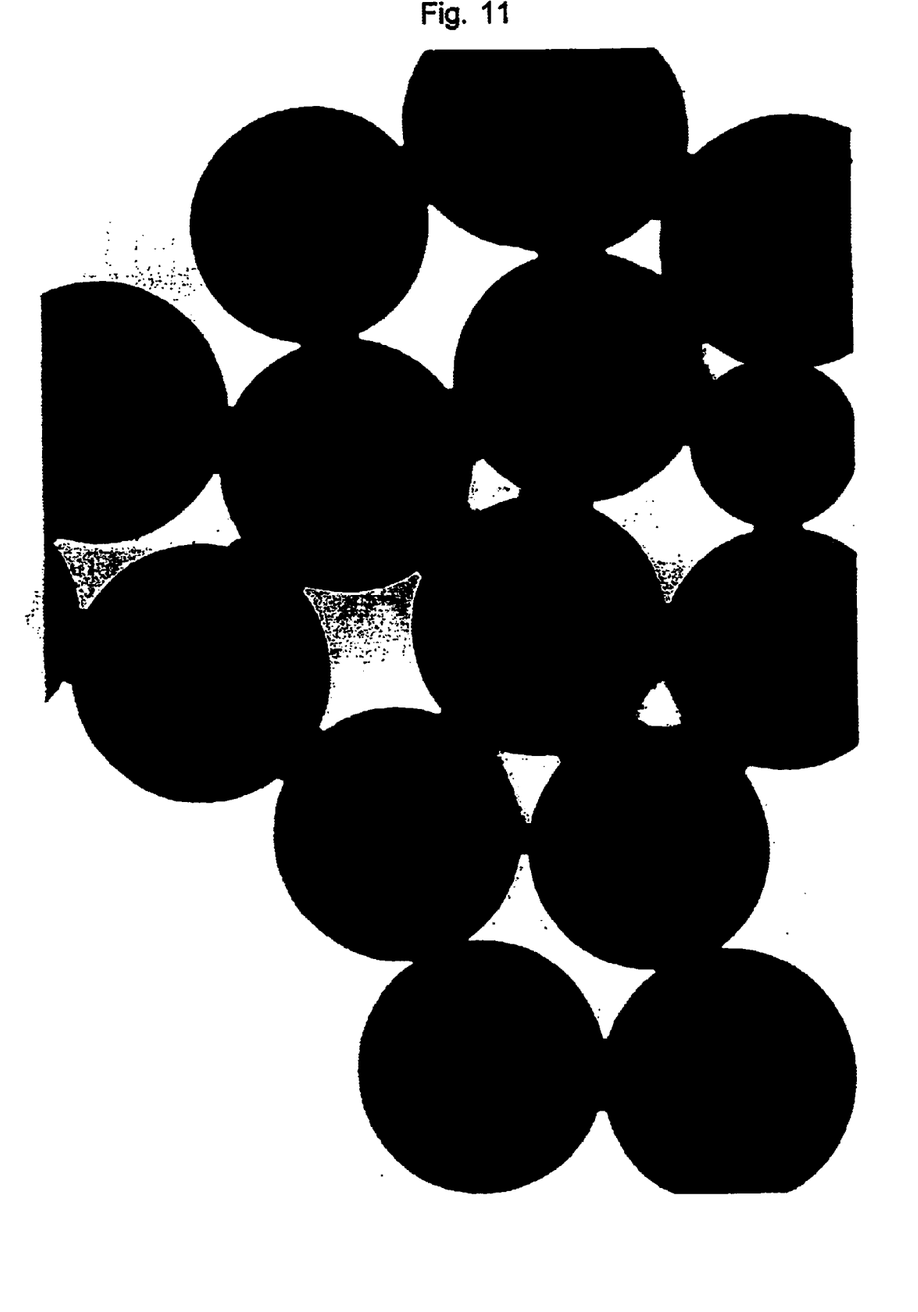
FIG. 11 is a photograph taken by Transmission Electron Microscopy (TEM) with a magnification of 100,000 of a spherical silica of 0.6 μm as used in examples 1–5 herein, showing that the spherical silica of the present invention is non-porous and there is no air void at the surface of or in the spherical silica.

As to the flaky, fine powder in Example 21, shown in FIG. 5 (magnified by 3500 times), the greater part of silica particles was separated, while as to the flaky, fine powder in Example 1, shown in FIG. 4 (magnified by 3500 times), there were no changes between the states before and after the stirring.

Preparation of the Cosmetic

EXAMPLE 22

The flaky, fine powder obtained in Example 1 and the following raw materials were compounded, and cake foundation was prepared.

| | |
|---|---|
| flaky, fine powder | 35.0 wt. % |
| talc | 25.0 wt. % |
| sericite | 20.0 wt. % |
| titanium oxide pigment | 10.0 wt. % |
| iron oxide pigment (red) | 1.4 wt. % |
| iron oxide pigment (black) | 0.2 wt. % |
| iron oxide pigment (yellow) | 2.9 wt. % |
| stearyl alcohol | 2.0 wt. % |
| lanolin | 2.0 wt. % |
| sorbitan fatty acid ester | 0.5 wt. % |
| triethanolamine | 1.0 wt. % |
| perfume | Suitable |

First, stearyl alcohol, lanolin, sorbitan fatty acid ester, triethanolamine, and perfume were mixed and heated to 80° C., and the rest of the powders mixed beforehand were added in the mixed liquid. This liquid was mixed sufficiently, then pressed and molded to cake foundation (Sample A).

EXAMPLE 23

The procedures were carried out in the same manner as described in Example 22 except that the flaky, fine powder obtained in Example 6 was used instead of that used in Example 22, and cake foundation was obtained (Sample B).

EXAMPLE 24

The procedures were carried out in the same manner as described in Example 22 except that the flaky, fine powder obtained in Example 7 was used instead of that used in Example 22, and cake foundation was obtained (Sample C).

COMPARATIVE EXAMPLE 1

The procedures were carried out in the same manner as described in Example 22 except that the natural mica non-covered with silica particles (used in Example 1) was used instead of the fine powder used in Example 22, and cake foundation was obtained (Sample D).

EXAMPLE 25

The flaky, fine powder obtained in Example 1 and the following raw materials were compounded, and milk foundation was prepared.

| | |
|---|---|
| flaky, fine powder | 18.0 wt. % |
| pure water | 61.1 wt. % |
| triethanolamine | 1.1 wt. % |
| methyl para-hydroxybenzoate | suitable |
| carboxymethylcellulose | 0.2 wt. % |
| bentonite | 0.5 wt. % |
| stearic acid | 2.4 wt. % |
| propylene glycol monostearate | 2.0 wt. % |
| cetostearyl alcohol | 0.2 wt. % |
| liquid paraffin | 3.0 wt. % |
| liquid lanolin | 2.0 wt. % |

-continued

| | |
|---|---|
| isopropyl myristate | 8.5 wt. % |
| propyl para-hydroxybenzoate | suitable |
| titanium oxide pigment | 1.0 wt. % |
| perfume | suitable |

First, carboxymethylcellulose was dispersed into pure water, then bentonite was added, and the dispersion was stirred sufficiently and heated to 70° C. Next, triethanolamine and methyl para-hydroxybenzoate were added in the dispersion, and a mixture comprising titanium oxide pigment and flaky, fine powder was added, then the mixed liquid was stirred sufficiently by a colloid mill and heated to 75° C.

Another mixture comprising stearic acid, propylene glycol monostearate, cetostearyl alcohol, liquid paraffin, liquid lanolin, isopropyl myristate, and propyl para-hydroxybenzoate was prepared, and the mixture was heated to 80° C., and stirred sufficiently with the above-mentioned mixed dispersion. This mixture was cooled, adding perfume at 45° C., and stirred at the room temperature, and then milk foundation was obtained (Sample E).

Evaluation of Cosmetic

Each of the samples A, B, C, D, and E described above was evaluated in terms of a degree of soft focus thereof as follows.

Each of the samples A to E was lightly applied to one face of a double-sided adhesive tape, respectively, and the tape was adhered to a white-color plate to be used as a test piece for measurement.

This test piece was set in a digital variable gloss meter (produced by Suga Shikenki, UGV-5D), light was irradiated onto the face on which the sample was applied at an incidence angle of 45 degrees, and scattering of reflected light was measured.

FIG. 6 through FIG. 10 are drawings showing distribution of reflected light for the sample A through E, respectively, and a quantity of reflected light when light is projected at a certain angle to the surface of a test piece is expressed with a length of a line segment as a relative value (%) against a quantity of reflected light from a reference plate (white-color plate on which no sample has been applied).

In any of sample A (FIG. 6), sample B (FIG. 7), sample C (FIG. 8), and sample E (FIG. 10), reflected light is distributed more homogeneously than in sample D (FIG. 9), which indicates that the soft focus effect in these samples is more excellent than in sample D.

Industrial Application

A surface of the flaky, fine powder according to the present invention is not a layer comprising irregular particles as that of flaky, fine powder according to the prior art, and is covered with spherical silica particles, so that the flaky, fine powder has particular functions which are different from those of the conventional type of flaky, fine powder. For this reason, the flaky, fine powder according to the present invention is useful as raw materials for such materials as a compounding agent for cosmetic and pigment, a filler for such materials as plastics, and a flat paint having low gloss and for providing a sense of high quality.

Especially, when used as a compounding agent for cosmetics it can reduce excessive gloss of mica as a base and provide a so-called soft focus effect, for instance, in making wrinkles invisible. Also with this flaky, fine powder according to the present invention, cosmetics having more excellent slipperiness and feeling as compared to the conventional type of cosmetic can be obtained.

What is claimed is:

1. A method of producing a flaky fine powder, comprising:
    adding alkoxysilane and/or silicic acid solution to a dispersion containing a flaky or scaly base and spherical silica particles, and
    immobilizing said spherical silica particles on the surface of said flaky or scaly base by hydrolyzing said alkoxysilane and/or gelling said silicic acid solution,
    said flaky or scaly base having a thickness of about 1 $\mu$m or less and is selected from the group consisting of mica, talc and platelet shaped silica, and said spherical silica particles comprise $SiO_2$ or a mixture of $SiO_2$ with one or more of $Al_2O_3$, $ZrO_2$, MgO, ZnO, $CeO_2$ or $Fe_2O_3$, said spherical silica particles being non-porous and having an average particle size of 0.05–3 $\mu$m,
    wherein the permittivity ($\in$) of said dispersion is in the following range:

$$15 \leq \in \leq 80$$

and the ion concentration (N) of the sun of cations and anions in said dispersion satisfies the following conditions:
(a) 200 ppm$\leq$N$\leq$5*$10^4$ ppm, when $\in$ is 15,
(b) 3*$10^4$ ppm$\leq$N$\leq$2*$10^5$ ppm, when $\in$ is 80, and
(c) N is in a quadrilateral area formed by A (15, 200), B (15, 5*$10^4$), C (80, 2*$10^5$) and D (80, 3*$10^4$) in the (X, Y) coordinate system with the X axis for the permittivity ($\in$) (–) and the Y axis for the ion concentration (N) (ppm), when $15 \leq \in \leq 80$.

2. A method of producing a flaky fine powder comprising:
    (a) dispersing a flaky or scaly base having a thickness of about 1 $\mu$m or less selected from the group consisting of mica, talc and platelet shaped silica, and spherical silica particles comprised of $SiO_2$ or a mixture of $SiO_2$ with one or more of $Al_2O_3$, $ZrO_2$, MgO, ZnO, $CeO_2$ or $Fe_2O_3$, in a dispersion medium comprising an organic solvent and/or water, to adhere said spherical silica particles on the surface of said flaky or scaly base, and
    (b) adding alkoxysilane and/or silicic acid solution to the obtained dispersion,
    said spherical silica particles being non-porous and having an average particle size of 0.05–3 $\mu$m and immobilized on the surface of said flaky or scaly base by hydrolyzing said alkoxysilane and/or gelling said silicic acid solution,
    wherein the permittivity ($\in$) of said dispersion is in the following range:

$$15 \leq \in \leq 80$$

and the ion concentration (N) of the sum of cations and anions in said dispersion satisfies the following conditions:
(a) 200 ppm$\leq$N$\leq$5*$10^4$ ppm when $\in$ is 15,
(b) 3*$10^4$ ppm$\leq$N$\leq$2*$10^5$ ppm, when $\in$ is 80, and
(c) N is in a quadrilateral area formed by A (15, 200), B (15, 5*$10^4$), C (80, 2*$10^5$) and D (80, 3*$10^4$) in the (X, Y) coordinate system with the X axis for the permittivity ($\in$) (–) and the Y axis for the ion concentration (N) (ppm), when $15 \leq \in \leq 80$.

3. A method of producing a flaky fine powder comprising:
    dispersing (a) a flaky or scaly base having a thickness of about 1 $\mu$m or less selected from the group consisting of mica, talc and platelet shaped silica, and (b) spherical silica particles comprised of $SiO_2$ or a mixture of $SiO_2$ with one or more of $Al_2O_3$, $ZrO_2$, MgO, ZnO, $CeO_2$ or $Fe_2O_3$, in a dispersion medium, said spherical silica particles being non-porous and having an average particle size of 0.05–3 μm, said spherical silica particles being deposited on a surface of said flaky or scaly base in said dispersion medium, and a flaky, fine powder being obtained by filtering, washing and drying the obtained dispersion, wherein the permittivity (∈) of said dispersion is in the following range:

$$15 \leq \in \leq 80$$

and the ion concentration (N) of the sum of cations and anions of said dispersion satisfies the following conditions, 200 ppm≦N≦5*10⁴ ppm, when ∈ is 15, 3*10⁴ ppm≦N≦2*10⁵ ppm, when ∈ is 80, and N is in a quadrilateral area formed by A (15, 200), B (15, 5*10⁴), C (80, 2*10⁵) and D (80, 3*10⁴) in the (X, Y) coordinate system with the X axis for the permittivity (∈) (–) and the Y axis for the ion concentration (N) (ppm), when 15≦∈≦80.

4. The method according to claim 3, further comprising immobilizing said spherical silica particles on the surface of said flaky or scaly base by adding alkoxysilane and/or silicic acid solution to said dispersion.

5. The method according to claim 3, further comprising immobilizing said spherical silica particles on said surface of said flaky or scaly base by adding alkoxysilane to said dispersion and hydrolysing said alkoxysilane.

6. The method according to claim 5, wherein said alkoxysilane is a compound having the formula:

Si(OR)₄, wherein R is an alkyl group with a carbon number of 1 to 7.

7. The method according to claim 3, further comprising immobilizing said spherical silica particles on the surface of said flaky or scaly base by adding silicic acid solution to said dispersion, and gelling said solution.

8. A method of producing a flaky fine powder comprising:

hydrolyzing tetraethoxysilane in a dispersion containing mica flakes having a thickness of about 1 μm or less, to thereby precipitate the silica and immobilize said silica on the surface of said mica flakes non-porous spherical silica particles having an average particle size of 0.05–3 μm, wherein the permittivity ∈ of said dispersion is in the following range;

$$15 \leq \in \leq 80$$

and the ion concentration (N) of the sun of cations and anions in said dispersion satisfies the following conditions, (a) 200 ppm≦5*10⁴ ppm, when ∈ is 15, (b) 3*10⁴ ppm≦N≦2*10⁵ ppm, when ∈ is 80, and (c) N is in a quadrilateral area formed by A (15, 200), B (15, 5*10⁴), C (80, 2*10⁵) and D (80, 3*10⁴) in the (X, Y) coordinate system with the X axis for the permittivity (∈) (–) and the Y axis for the ion concentration (N) (ppm), when 15≦∈≦80.

9. A flaky, fine powder comprising a flaky or scaly base having a thickness of about 1 μm or less and selected from the group consisting of mica, talc and platelet shaped silica; and spherical silica particles comprised of SiO₂ or a mixture of SiO₂ with one or more of Al₂O₃, ZrO₂, MgO, ZnO, CeO₂ or Fe₂O₃, and said spherical silica particles being non-porous and having an average particle size of 0.05–3 μm and covering the surface of said flaky or scaly base.

10. The flaky, fine powder according to claim 9, wherein said spherical silica particles are immobilized on the surface of said flaky or scaly base by a hydrolysate of alkoxysilane and/or silica gel.

11. A flaky, fine powder comprising a flaky or scaly base having a thickness of about 1 μm or less selected from the group consisting of mica, talc and platelet shaped silica; and spherical silica particles comprised of SiO₂ or a mixture of SiO₂ with one or more of Al₂O₃, ZrO₂, MgO, ZnO, CeO₂ or Fe₂O₃, and said spherical silica particles being non-porous and having an average particle size of 0.05–3 μm which adhere to the surface of said flaky or scaly base.

12. The flaky, fine powder according to claim 11, wherein said spherical silica particles are immobilized on said flaky or scaly base by hydrolysate of alkoxysilane, and/or silica gel.

13. A cosmetic comprising a flaky fine powder produced according to the method of claim 3.

14. A cosmetic comprising a flaky fine powder produced according to the method of claim 1.

15. A cosmetic comprising a flaky fine powder produced according to the method of claim 2.

16. A cosmetic comprising a flaky, fine powder as claimed in claim 9.

17. A cosmetic comprising a flaky, fine powder as claimed in claim 10.

18. A cosmetic comprising a flaky, fine powder as claimed in claim 11.

* * * * *